United States Patent
Monfre et al.

(10) Patent No.: US 6,675,029 B2
(45) Date of Patent: *Jan. 6, 2004

(54) APPARATUS AND METHOD FOR QUANTIFICATION OF TISSUE HYDRATION USING DIFFUSE REFLECTANCE SPECTROSCOPY

(75) Inventors: Stephen L. Monfre, Gilbert, AZ (US); Timothy L. Ruchti, Gilbert, AZ (US); Thomas B. Blank, Chandler, AZ (US); Brian J. Wenzel, Cave Creek, AZ (US)

(73) Assignee: Sensys Medical, Inc., Chandler, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/183,660

(22) Filed: Jun. 25, 2002

(65) Prior Publication Data

US 2003/0060693 A1 Mar. 27, 2003

Related U.S. Application Data

(63) Continuation-in-part of application No. 09/669,781, filed on Sep. 25, 2000, now Pat. No. 6,442,408, which is a continuation-in-part of application No. 09/359,191, filed on Jul. 22, 1999, now Pat. No. 6,280,381.

(51) Int. Cl.[7] ................................................. A61B 5/00
(52) U.S. Cl. ..................... 600/310; 600/473; 250/339.1; 250/341.8
(58) Field of Search ................................. 600/310, 322, 600/473, 475; 356/303; 250/339.01, 339.07, 339.09, 339.1, 339.11, 340, 341.5, 341.8

(56) References Cited

U.S. PATENT DOCUMENTS 6,442,408 B1 * 8/2002 Wenzel et al. .............. 600/310

FOREIGN PATENT DOCUMENTS

CA            2210791        * 1/1999

* cited by examiner

Primary Examiner—Eric F. Winakur
(74) Attorney, Agent, or Firm—Glenn Patent Group; Michael A. Glenn; Christopher Feil

(57) ABSTRACT

An apparatus and method for non-destructively estimating a tissue property, such as hydration, of a living subject utilizes in vivo spectral measurements made by irradiating skin tissue with near infrared (NIR) light. The apparatus includes a spectroscopic instrument in conjunction with a subject interface. The resulting spectra are passed to an analyzer for further processing, which includes detecting and eliminating invalid spectral measurements, and preprocessing to increase the signal-to-noise ratio. Finally, an estimation model developed from an exemplary set of measurements is applied to predict the tissue hydration for the sample. The method of tissue hydration measurement provides additional information about primary sources of systematic tissue variability, namely, the water content of the epidermal layer of skin and the penetration depth of the incident light. Tissue hydration measurement is therefore suitable for further spectral analysis and quantification of biological and chemical compounds, such as analytes.

48 Claims, 6 Drawing Sheets

APPARATUS AND METHOD FOR QUANTIFICATION OF TISSUE HYDRATION USING DIFFUSE REFLECTANCE SPECTROSCOPY

CROSS REFERENCE TO RELATED APPLICATION

This application is a Continuation-in-part of U.S. patent application Ser. No. 09/669,781, filed Sep. 25, 2000, now U.S. Pat. No. 6,442,408, which is a Continuation-in-part of U.S. patent application Ser. No. 09/359,191, filed Jul. 22, 1999, now U.S. Pat. No. 6,280,381, issued on Aug. 28, 2001.

BACKGROUND OF THE INVENTION

1. Field of the Invention

The invention relates to the use of spectroscopy to characterize living tissue. More particularly, the invention relates to an apparatus and method for quantifying tissue hydration in a living subject non-destructively, based on irradiation of the skin tissue with near infrared light energy.

2. Description of Related Art

Near infrared (NIR) tissue spectroscopy is a promising nondestructive technology that bases measurements on the irradiation of a tissue site with NIR energy in the 700–2500 nanometer wavelength range. The energy is focused onto an area of the skin and propagates according to the scattering and absorption properties of the skin tissue. Therefore, the reflected or transmitted energy that escapes and is detected provides information about the tissue volume that is encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and blood analytes absorb light approximately proportionally to their concentration through unique absorption profiles or signatures. The measurement of tissue properties, characteristics or composition is based on detecting the magnitude of light attenuation resulting from its respective scattering and/or absorption properties.

Stratum Corneum Hydration Measurement

The quantification of hydration of the stratum corneum has commercial benefits in certain industries for monitoring skin condition and for attaining a better understanding of how hydration affects the stratum corneum. The current method of measuring the hydration of the stratum corneum non-invasively is based on the electrical characteristics of the stratum corneum. The technology measures the capacitance, admittance, impedance, or susceptance of the stratum corneum.

Spectroscopic approaches to measuring hydration of the stratum corneum have been explored. See, for example, R. Potts, D. Guzek, R. Harris, J. McKie, *A Noninvasive, In Vivo Technique to Quantitatively Measure Water Concentration of the Stratum Corneum Using Attenuated Total-Reflectance Infrared Spectroscopy*, Archives of Dermatological Research, Springer-Verlag, vol. 277, (1985). Potts, et al. performed a variety of in vitro experiments using Attenuated Total Reflectance (ATR) spectroscopy in the infrared region of light, and determined that hydration of the skin was highly correlated (0.99) to the ambient humidity. He developed a variety of preprocessing techniques like the protein ratio and the moisture factor to measure the hydration of the stratum corneum. He concluded that water content in the stratum corneum could be measured in vitro using ATR infrared spectroscopy. The Potts teachings however are directed to an in vitro method and are therefore unsuited to noninvasive, in vivo measurements.

Martin did a series of experiments related to in vivo measurement using diffuse reflectance near infrared spectroscopy. See K. Martin, *Direct Measurement of Moisture in Skin by NIR Spectroscopy*, Journal of Society of Cosmetic Chemists, vol. 44 (1993). Martin's work lead to the finding that three different types of water may be detected in the spectra of skin. The different types of water were found in the overtone region (1058–1950 nm) using the second derivative of the spectrum; second derivative intensities were found to correlate with ambient humidity levels. It was found that the bulk water of the stratum corneum correlates most directly with ambient humidity. Bulk water was water that mostly resembled that of regular water and was not bound to any protein. It was also found that the primary hydration water correlated the least with ambient humidity.

Martin's further work investigated the use of measuring sites at a variety of body locations having skin of varying thickness. See K. Martin, *In Vivo Measurements of Water in Skin by Near Infrared Reflectance*, Applied Spectroscopy, vol. 52(7)(1998). While a higher standard deviation was noted, the previous correlations with different water types in the skin were confirmed. Additionally, light scattering by the skin was found to decrease with increasing hydration. The Martin teachings, however, do not address the persistent problem in the art of compensating for structural and physiological variation between individuals or variation over time within the same individual.

Analyte Estimation

While noninvasive estimation of analytes, such as glucose concentration, has been pursued through NIR spectroscopy, the reported success and product viability has been limited by the lack of a system for compensating for structural variations between individuals that produce dramatic changes in the optical properties of the tissue sample. For example, see O. Khalil, *Spectroscopic and clinical aspects of non-invasive glucose measurements*, Clin Chem, vol. 45, pp 165–77 (1999) or J. Roe, B. Smoller, *Bloodless Glucose Measurements, Critical Reviews in Therapeutic Drug Carrier Systems*, vol. 15, no. 3, pp. 199–241, 1998. These differences are largely anatomical and provide distinct systematic spectral absorbance features or patterns that can be related directly to specific characteristics such as dermal thickness, protein levels and hydration. While the absorbance features are repeatable within a subject, over a population of subjects they produce confounding nonlinear spectral variation. Therefore, differences between subjects are a significant obstacle to the noninvasive measurement of analytes through NIR spectral absorbance.

A related U.S. Patent Application, S. Malin, T. Ruchti, An intelligent system for noninvasive blood analyte prediction, U.S. patent application Ser. No. 09/359,191 (Jul. 22, 1999), now U.S. Pat. No. 6,280,381, discloses an apparatus and procedure for substantially reducing this problem by classifying subjects according to major skin tissue characteristics prior to blood analyte estimation. The selected characteristics are representative of the actual tissue volume irradiated and the amount of the target analyte that is sampled. By grouping individuals according to the similarity of spectral characteristics representing the tissue structure, the nonlinear variation described above is reduced and estimation of analytes becomes more accurate.

SUMMARY OF THE INVENTION

The present invention provides a novel apparatus and related procedures for the quantification of hydration of the tissue through NIR tissue spectroscopy having particular benefit in several areas, including tissue state evaluation and analyte estimation. The invention utilizes a spectroscopic technique such as NIR diffuse reflectance to measure the hydration of the stratum corneum. A spectroscopic apparatus in conjunction with an optical subject interface is used to measure tissue properties and characteristics non-destructively, that are manifested spectrally and vary systematically according to the hydration of the subject's stratum corneum.

The procedure for quantifying tissue hydration, particularly the stratum corneum, involves a calibration model that is empirically derived from a set of exemplary samples consisting of NIR tissue measurements and corresponding independent measurements made with a corneometer. The model is a set of parameters and computer generated code that is implemented to predict the hydration of the subject's stratum corneum. The general procedure involves the steps of taking spectral measurements, typically in the near IR region of 700 to 2500 nm; detecting outliers, invalid measurements resulting from poor sampling technique, or instrument problems, or a subject outside of the calibration set; preprocessing, in which the spectral measurements are subjected to various operations that attenuate noise and instrumental variation; and estimation, in which the previously mentioned calibration model is applied to arrive at an estimation of the hydration of the subject's stratum corneum.

DETAILED DESCRIPTION

Figure 1:
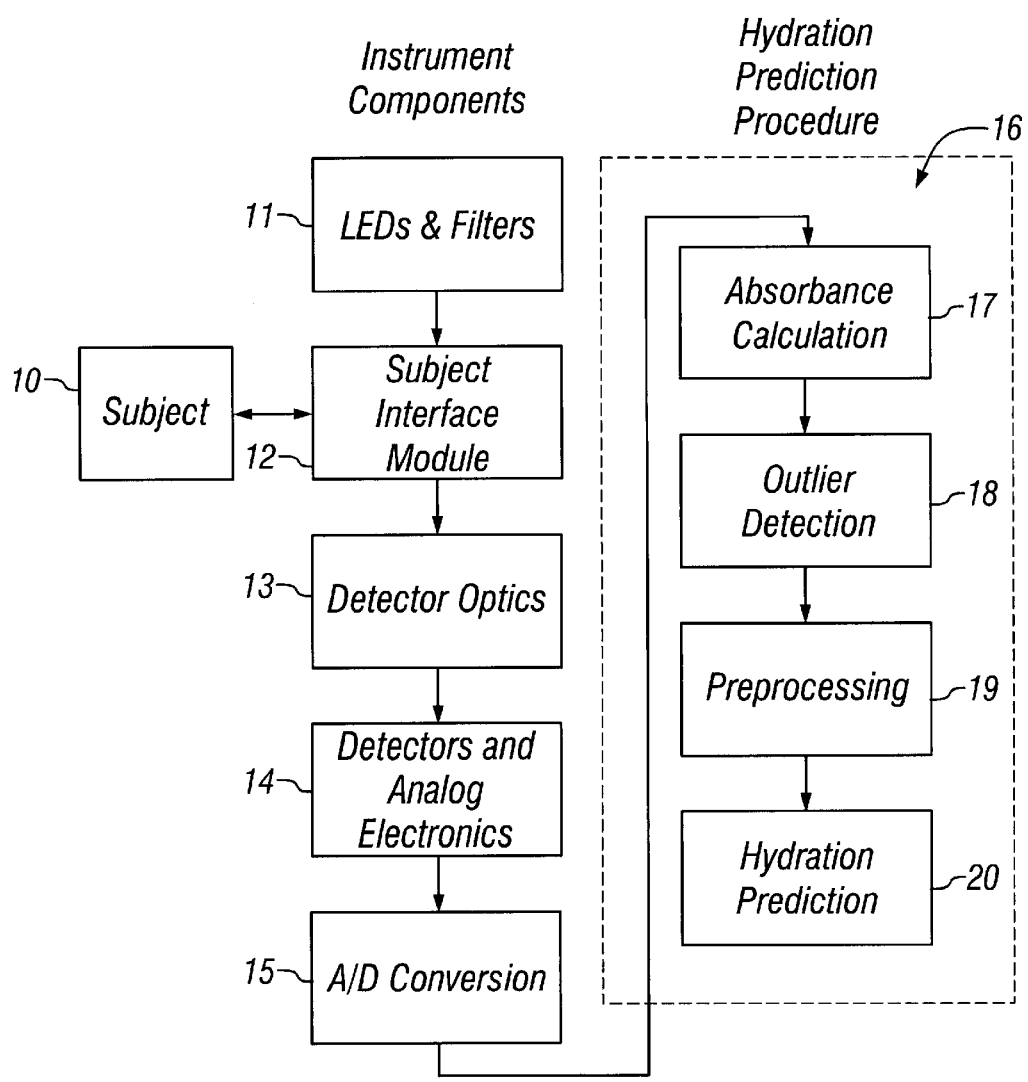
FIG. 1 provides a block diagram of a system for predicting stratum corneum hydration, according to the invention.

The system for quantifying the hydration of a tissue such as the stratum corneum non-destructively provides an apparatus for measuring the near infrared absorption by tissue irradiated with near infrared energy and a procedure for determining the tissue's hydration. Although the invented apparatus and procedure are described herein with respect to quantifying hydration of the stratum corneum (SC), this description is intended to be exemplary only. One skilled in the art will recognize that the invention has application in quantifying hydration of other tissue components of skin besides the stratum corneum: the epidermis, the dermis, and the subcutaneous layer, for example. Additionally, the invented apparatus finds utility in a large number of other applications, among them:

Body fat determination;
Body composition determination;
Determining thickness of the subcutaneous layer;
Estimating chronological age of a subject;
Assessing photo-aging of the skin;
Assessing photo-damage to the skin;
Determining tissue hydration;
Measuring skin temperature;
Determining skin thickness;
Characterizing body fat;
Skin cancer detection;
Estimating blood volume;
Determining tissue circulation and rate of perfusion;
Determining tissue turgor;
Determining tissue elasticity;
Determining edema in tissue;
Sex determination;
Determining dermis hydration level;
Determining epidermis hydration level;
Assessing tissue deformity;
Determining tissue cholesterol;
Assessing sweat;
Assessing free and bound water;
Determination of the relative and absolute concentration of water in the extracellular and intracellular fluid;
Determination of the relative and absolute concentration of water in the interstitial fluid;
Determination of the relative and absolute concentration of water in the extravascular and intravascular compartments;
Assessing orientation of collagen fibers; and
Tissue analyte determination, including at least: glucose, alcohol, cholesterol, triglycerides, sodium, urea, elastin and collagen.

Hydration Estimation Apparatus

The apparatus includes an energy source 11, one or more sensor elements, an interface 12 to the subject 10, a means for wavelength selection and an analyzer. The source generates and transmits near-infrared energy in the wavelength range of 700–2500 nanometers. In a preferred embodiment, the source 11 and the wavelength selection means constitute a LED (light emitting diode) array 11 and successive illumination through the elements of the LED array 11. Alternatively, the source may constitute a light source, such as a quartz halogen lamp, and the wavelength selection means may constitute any of a spectrometer, a spectrograph, a monochromator or an interferometer (not shown). In the preferred embodiment, wavelength selection occurs before the tissue is irradiated. Thus, the energy reaching the tissue constitutes monochromatic light. However, an embodiment is also possible in which the tissue is irradiated by polychromatic light, for example from an LED array emitting polychromatic light. In such case, wavelength selection occurs after the tissue is irradiated, prior to being detected by the sensor elements. The sensor elements are detectors 14 that are responsive to a set of targeted wavelengths. The interface to the subject comprises a means of transmitting energy from the source 11 to a target skin tissue measurement site and includes, for example, direct illumination, a light pipe, fiber-optic probes, a lens system or a light directing mirror system. Energy is collected from the surrounding tissue areas in reflectance mode at an optimally determined distance(s) through the use of detector optics 13 or fiber optics. Alternately, energy is collected in a transmission mode through a skin fold, ear lobe, finger or other extremity. The collected light, constituting an analog signal is converted to a current by the sensor elements 14 and sampled through an analog-to-digital converter 15 for analysis on a data processing system.

Figure 4:
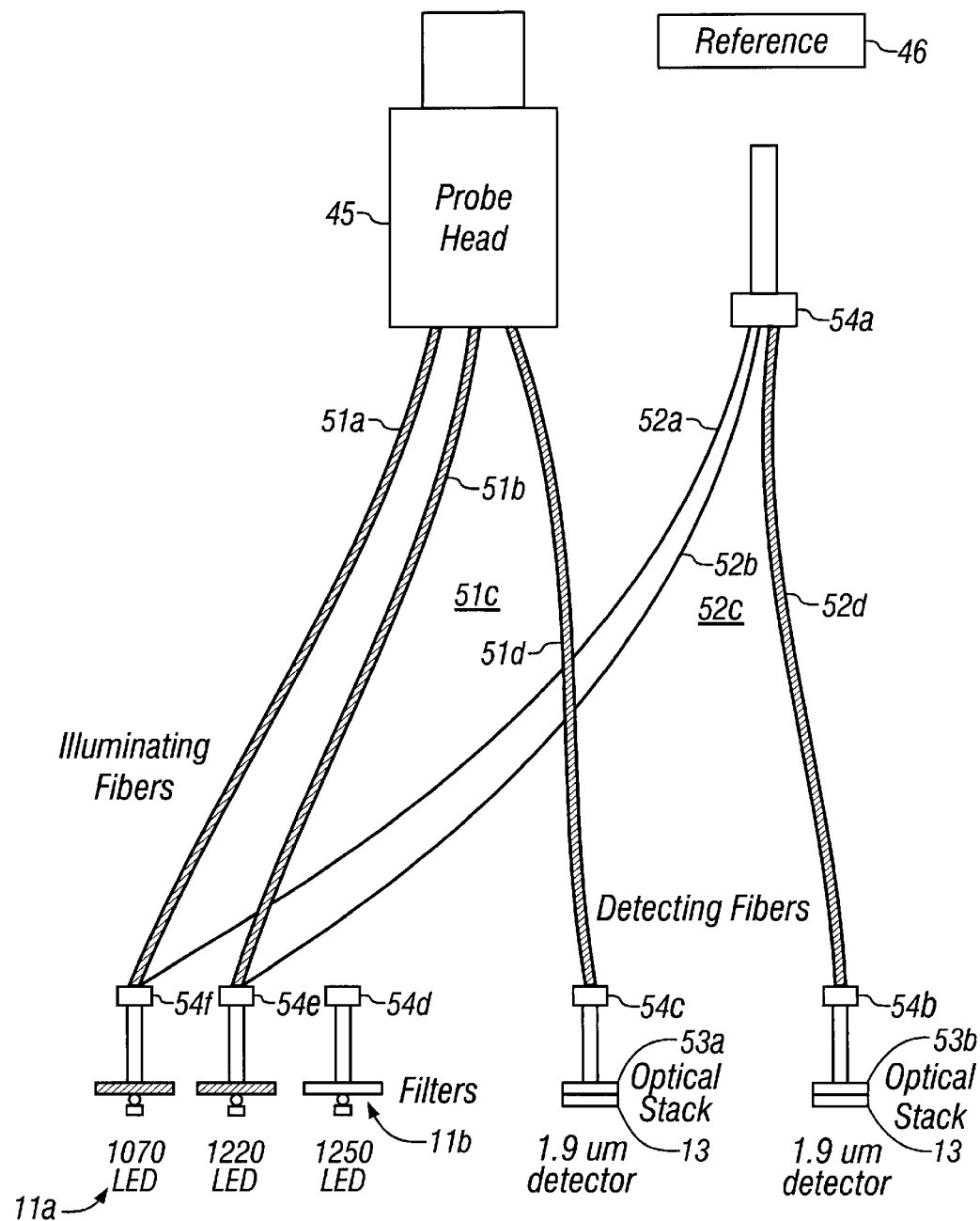
FIG. 4 illustrates an arrangement of illumination and detection fibers in the hydration meter of FIG. 3, according to the invention.

In the preferred embodiment, a group of LED's 11 is employed to transmit energy of pre-selected wavelengths to the skin; the LED's are radially surrounded by detection fibers 13 at specific distances. The LED's are alternately energized and the detected energy of each LED reflected or transmitted through the skin is used to form one spectrum. The edge-to-edge distance between each of the LED's and the detector elements, or the distance between the point of illumination, comprising the light-emitting surface of the LED's, and the point of detection is a minimum of 40 $\mu$m and a maximum of 1 mm. Distances of less than 40 $\mu$m produce too much surface reflection of the NIR radiation and distances of greater than 1 mm result in too much penetration of the NIR radiation. The set of wavelengths includes 1070, 1180, 1280 nm and 1110, 1190, and 1280 nm. However, other wavelength ranges, corresponding to water bands in the NIR absorbance spectrum, are also suitable. Coupling of the illumination and detector elements, shown in detail in FIG. 4, is accomplished through fiber optics. One skilled in the art will appreciate that other coupling methods are suitable, including direct illumination/detection, optics and lens systems, subject to the criterion for the distances between the point of illumination and detection. The detected intensity from the sample is converted to a current through analog electronics 14 and digitized through an analog-to-digital converter (ADC) 15. The spectrum is passed to the hydration estimation procedure 16 for processing. First, the absorbance is calculated 17 on the basis of the detected light through $-\log(R/R_0)$ where R is the reflected light and $R_0$ is the light incident on the sample determined by scanning a reference standard. Subsequent processing steps, described below, result in either hydration estimation or a message indicating an invalid scan. A block diagram of the integrated system is shown in FIG. 1.

Alternately, the measurement can be accomplished with existing NIR spectrometers that are commercially available, including a FOSS-NIR Systems NIRS 5000 spectrometer, provided by FOSS NIR SYSTEMS, INC. of Eden Prairie Minn., or a Nicolet Magna-IR 760 spectrometer, provided by THERMO NICOLET, INC of Madison Wis. In addition, the measurement can be made by collecting reflected light off the surface of the skin or light transmitted through a portion of the skin, such as the finger or the ear lobe. Further, the use of transmittance to determine absorbance can replace the preferred reflectance measurement. In addition, intensity can be used to replace absorbance. In the transmittance configuration, the spacing of the illumination and detection fibers is performed on the basis of the skin fold or tissue through which NIR radiation is transmitted.

Estimation Procedure

The general procedure for quantifying hydration based on the measured spectrum, shown in FIG. 1, is implemented in a data processing system such as a microcomputer 44 that automatically receives the measurement information from the ADC 15. The hydration quantifying procedure comprises a series of steps, including outlier detection 18 (optional), preprocessing 19, and estimation 20 wherein each step is a procedure in itself. Each procedure relies on a calibration set of exemplary measurements. Herein below, the general steps of the Hydration Estimation Procedure are summarized, with a detailed description following in the subsequent section titled "Implementation."

Measurement (17)

Figure 2:
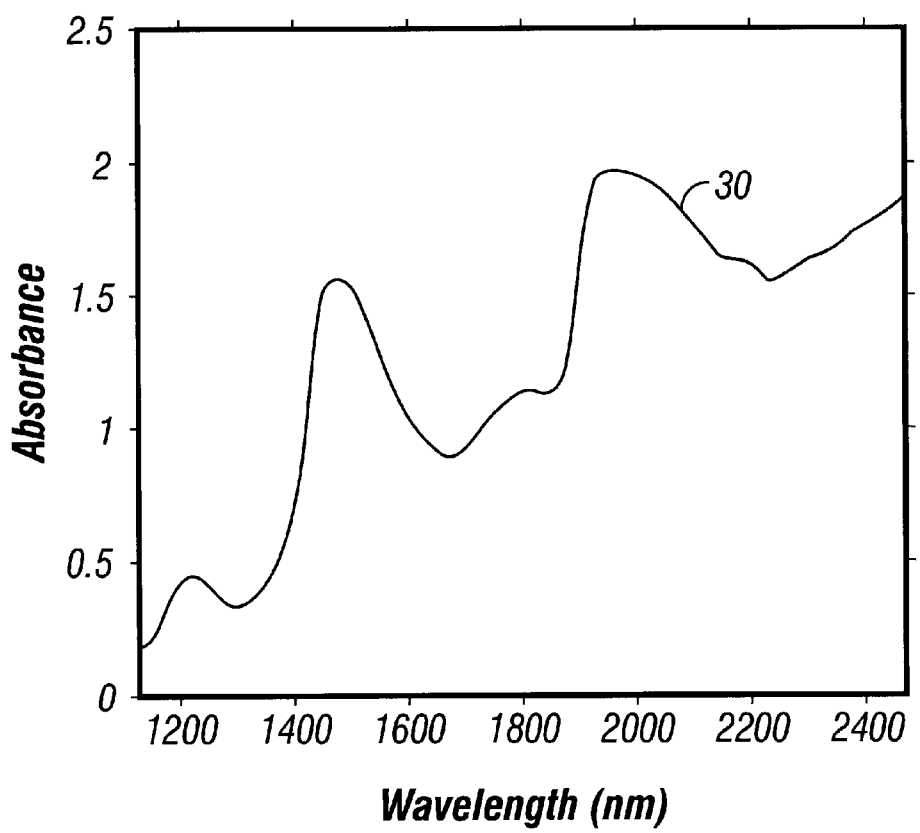
FIG. 2 illustrates a typical noninvasive NIR absorbance spectrum.

The measurement is a spectrum denoted by the vector $m \in R^N$ of absorbance values pertaining to a set of N wavelengths $\lambda \in R^N$ that span the near infrared (700 to 2500 nm). A typical plot 30 of m versus $\lambda$ is shown in FIG. 2.

Outlier Detection (18)

The outlier detection procedure provides a method of detecting invalid measurements through spectral variations that result from problems in the instrument, poor sampling of the subject or a subject outside the calibration set. The preferred method for the detection of spectral outliers is through a principal component analysis and an analysis of the residuals. See H. Martens, T. Naes, *Multivariate Calibration*, John Wiley & Sons, New York (1989). First, the spectrum, m, is projected onto five eigenvectors, contained in the matrix o, that were previously developed through a principal components analysis (on a calibration set of exemplary absorbance spectra) and are stored in the computer system of the device. The calculation is given by $$xpc_o = \sum_{k=1}^{5} mo_k \tag{1}$$

and produces the 1 by 5 vector of scores, $xpc_o$, where $o^k$ is the $k^{th}$ column of the matrix o. The residual, q, is determined according to $$q = m - xpc_o o^T \tag{2}$$

and compared to three times the standard deviation of the expected residual (of the calibration set). If greater, the sample is reported to be an outlier and the hydration measurement procedure is terminated.

Preprocessing (19)

Preprocessing includes operations such as scaling, normalization smoothing, derivatives, filtering and other transformations that attenuate the noise and instrumental variation without affecting the signal of interest. The preprocessed measurement, $x \in R^N$, is determined according to $$x = h(\bar{e}, m) \tag{3}$$

where h: $R^{N \times 2} \to R^N$ is the preprocessing function.

Estimation (20)

Estimation may include operations such as multiple linear least squares regression (MLR), principle component regression (PCR), and partial least squares regression (PLR) analysis that process the measurement, $y \in R^N$, according to $$y = g(x) \tag{4}$$

where g: $R^N \to R^1$ is the regression function.

Implementation Details

This section describes a particular embodiment of the apparatus and specific procedures for quantifying tissue characteristics, and in particular, tissue hydration. The structure of the procedures relies on a priori knowledge of the systematic variation of the skin structure, namely, the hydration state of the stratum corneum and the variation in path depth of the irradiated light. However, the parameters of each procedure, such as the eigenvectors for outlier detection, are determined on the basis of an experimental data set, the "calibration set", providing exemplary information.

Apparatus

Figure 3:
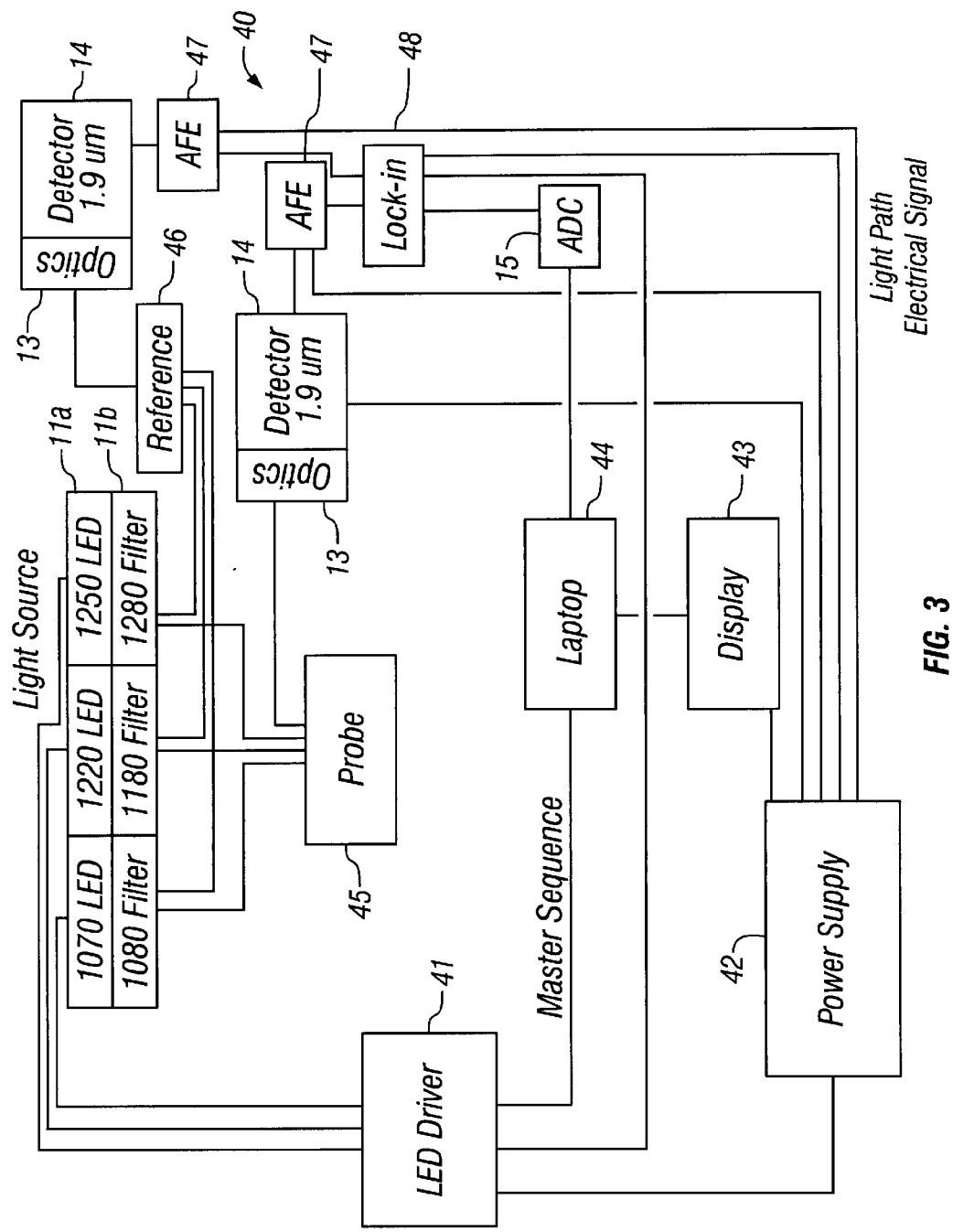
FIG. 3 provides a block diagram of a hydration meter, according to the invention.

FIG. 3 provides a block diagram for the hydration meter 40. The light source 11 for this device includes an array 11a of three light emitting diodes (LED's). The current source for the LED's is an LED driver 41 connected to a power supply 42 that pulses the LED's at a frequency of between 1 kHz and 10 kHz. The LED driver 41 supplies a current of up to 3.0 amperes. The LED's used for this device have a peak wavelength at 1.07_m, 1.22_m, and 1.25_m. Each LED is equipped with a bandpass interference filter 11b; the bandpass interference filters of the preferred embodiment have center wavelengths of 1080 nm, 1180 nm, and 1280 nm, respectively, with their full width half maximum ranging from 11.0 to 14.8 nm. The light is transmitted to the probe heads 45, 46 via fiber optics 51a–c, 52a–c. FIG. 4 illustrates the coupling of the LED's 11a with the probe heads 45, 46 by means of fiber optics 51a–c, 52a–c.

Figure 5:
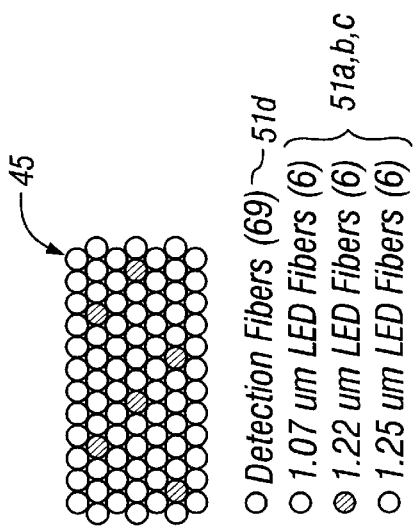
FIG. 5 illustrates an arrangement of illumination and detection fibers in a sample probe head of the hydration meter of FIG. 3, according to the invention.
Figure 6:
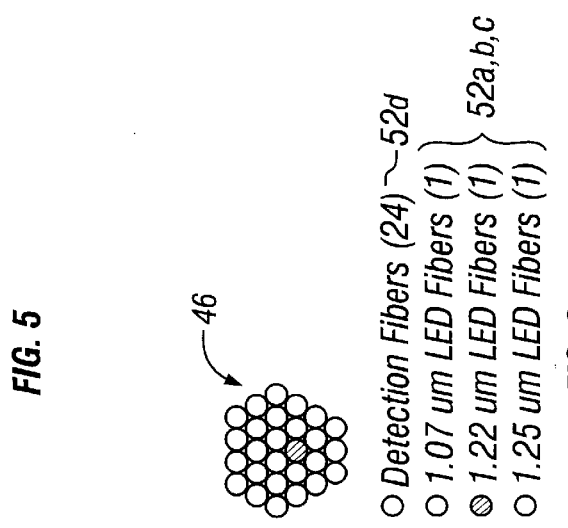
FIG. 6 illustrates an arrangement of illumination and detection fibers in a reference probe head of the hydration meter of FIG. 3, according to the invention.

Each LED has seven 100_m core diameter fiber optics associated with it. Six of these fiber optics 51a–c go to the sample probe head 45, and one 52a–c goes to the reference probe head 46. The sample probe head 45 is the subject interface 12 of the device that comes into contact with the stratum corneum. FIG. 5 shows a preferred fiber optic arrangement for the sample probe head 45, comprising a total of eighteen illuminating fibers 51a–c and sixty-nine detecting fibers 51d. Each illuminating fiber 51a–c is completely surrounded, in a closed, packed arrangement, by detection fibers 51d for greatest light collection. Shown in FIG. 6, the reference probe head 46 is used to collect a dual beam reference of an internal diffuse reflectance standard having known spectral characteristics. The reference probe has a total of three illuminating fibers 52a–c and from 20 to 30 detecting fibers 52d. The diffuse reflected light from each of the probe heads, sample and reference, travels via optical fibers 51d, 52d to an optical system 53a, b that focuses the light onto the 1.9_m InGaAs detectors 14. The fiberoptics are coupled to the various components with connecting elements 54a–f. In the preferred embodiment of the invention, the connecting elements 54 are brass connectors, but other equally suitable alternatives will be apparent to those skilled in the art.

The signals from the detectors are amplified in the analog front end 47 (AFE). The AFE also converts the current signal from the detectors to a voltage signal before transmitting the signal to the lock-in amplifier 48. The phase modulating lock-in amplifier 48 receives the signal from the AFE 47 and a reference signal from the LED driver 41. The lock-in amplifier 48 amplifies signals that are in phase with the reference signal. This increases the signal-to-noise ratio, and gives a DC (direct current) output. The output from the lock-in amplifier 48 goes through a 16-bit analog to digital converter (ADC) 15.

A laptop computer 44 or other analyzer receives the signal from the ADC 15, and predicts the hydration based on the invented algorithm 16 described further below. After the signal is processed, the estimation result is displayed on a display device 43 attached to the laptop 44. The laptop also controls the master sequence 49 on the LED's, controlling both of: which LED is emitting, and the time period for which each LED is emitting.

SC Hydration Estimation

The preferred analytical method for hydration estimation according to the invention is multiple linear regression (MLR); the estimation calculation is given by:

$$\overset{1}{y} = \acute{a}_1 x_1 + \acute{a}_2 x_2 + \acute{a}_3 x_3 + \acute{a} \tag{5}$$

where $$\overset{1}{y}$$

is the predicted hydration; $x_1$, $x_2$, and $x_3$ are the absorbance of each LED, $a_1$, $a_2$ and $a_3$ are the coefficients to the absorbance of each LED, and e is the error associated with the model. The coefficients are calculated by $$w = (x^t \cap x)^{-1} \cap x^t \cap y \tag{6}$$

where x is the matrix of absorbance values after the preprocessing techniques are complete, y is the corneometer readings for each spectral measurement, and w is the matrix containing the coefficients:

$$w = \begin{matrix} \acute{a}_1 \\ \acute{a}_2 \\ \acute{a}_3 \end{matrix} . \tag{7}$$

Absorbance is calculated 17 by:

$$m = -\log \frac{R}{R_o} \tag{8}$$

where m is the absorbance spectrum, R is the intensity signal from the sample probe head, and $R_0$ is the intensity signal from the reference probe head. The absorbance spectrum, m, is passed through the outlier detection system 18 to remove any bad measurements or readings outside the estimation model's range. After outlier detection, the signal is preprocessed 19 to attenuate any noise and instrumental variation. The preprocessing techniques employed are multiplicative scatter correction and mean centering. The spectrum is processed, using multivariate scatter correction through a rotation that fits it to the expected or reference spectrum $\bar{n}$, determined from the calibration set. See P. Geladi, D. McDougall, H. Martens, *Linearization and Scatter-Correction for Near-Infrared Reflectance Spectra of Meat, Applied Spectroscopy*, vol. 39, pp. 491–500 (1985). First, the spectrum is fitted via linear regression according to $$m = a + b\bar{m} + e \tag{9}$$

where a and b are the slope and intercept and e is the error in the fit. The spectrum is then corrected through:

$$x = \frac{m - a}{b} \tag{10}$$

where x is the processed absorbance spectrum. From this spectrum, the mean from an exemplary data set is calculated for each LED absorbance. The mean is then subtracted from each LED absorbance in the measured data set. After mean centering the data, it is passed through the multiple linear regression model described above for the estimation of SC hydration. For the current embodiment, the coefficients for the multiple regression model, $a_1$, $a_2$, and $a_3$, are 2411.4, –2486.6, and 257.2, respectively.

Other methods of developing a calibration model for the hydration of the stratum corneum may be used, for example, using factor analysis to develop a set of abstract features capable of representing the spectral variation related to hydration. For factor analysis, the spectral measurements, NIR absorbance spectra similar to that of FIG. 2, are used. The spectrum is sub-divided into one or more regions according to wavelength (wavelength selection) and is pre-processed and normalized to enhance spectral variation related to SC hydration. The measurements are projected onto one or more sets of previously determined factors (eigenvectors) to determine the scores. The scores constitute the extracted features and are subjected to an estimation procedure, such as linear discriminate analysis, SIMCA, k nearest-neighbor, fuzzy classification and various forms of artificial neural networks to predict hydration of the stratum corneum. See R. Duda, P. Hart, *Pattern Classification and Scene Analysis*, John Wiley & Sons, New York (1973) or S. Wold, M. Sjostrom, *SIMCA: A method for analyzing chemical data in terms of similarity and analogy, Chemometrics: Theory and Application*, ed. B. R. Kowalski, ACS Symposium Series, vol. 52 (1977) or J. Bezdek, S. Pal, eds., *Fuzzy Models for Pattern Recognition*, IEEE Press, Piscataway, N.J. (1992) or J. Keller, M. Gray, J. Givens, *A fuzzy k nearest neighbor algorithm, IEEE Transactions on Systems, Man, and Cybernetics*, vol. SMC-15(4), pp. 580–585, (July/August, 1985) or Y. Pao, *Adaptive Pattern Recognition and Neural Networks*, Addison-Wesley Publishing Company, Reading, Mass. (1989).

Experimental Data Set

A study was performed to develop a calibration model for predicting SC hydration. The spectroscopic measurements were made using a spectrometer instrument according to an embodiment of the invention, comprising a quartz lamp, a monochromator, a fiber optic probe, and a detector set-up. The study consisted of four human subjects (3 males and 1 female), in which the hydration of the SC at the measurement site was modified through occlusion of the skin. Different occlusion times were employed to develop a range of hydration values, with no treatment of the skin at the sampling site prior to measurement. Stratum corneum hydration was measured independently by the corneometer CM 825, produced by COURAGE & KHAZAKA of Cologne, Germany. Each subject had a minimum of eight spectral scans with corresponding corneometer readings over a period of at least two days in duration, each scan constituting a sample. The spectral measurements and the corresponding corneometer readings are referred to as the "Experimental Data Set" herein below.

Feasibility

Figure 7:
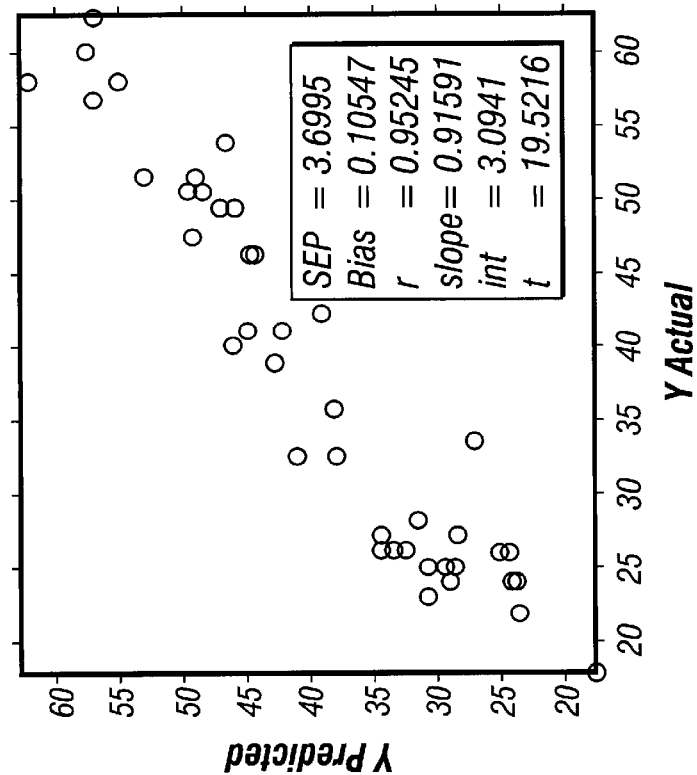
FIG. 7 shows a plot of actual SC hydration measurements vs. estimations in a calibration model for predicting SC hydration, according to the invention.
Figure 8:
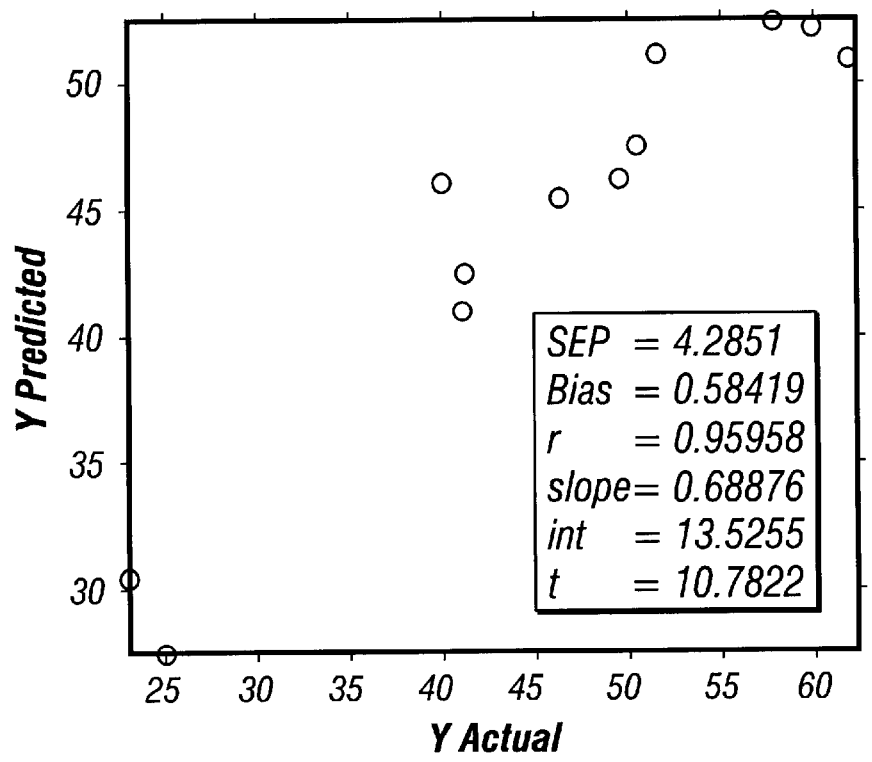
FIGS. 8 and 9 show plots of actual SC hydration measurements vs. predicted for two different subjects, based on the calibration model of FIG. 7, according to the invention.
Figure 9:
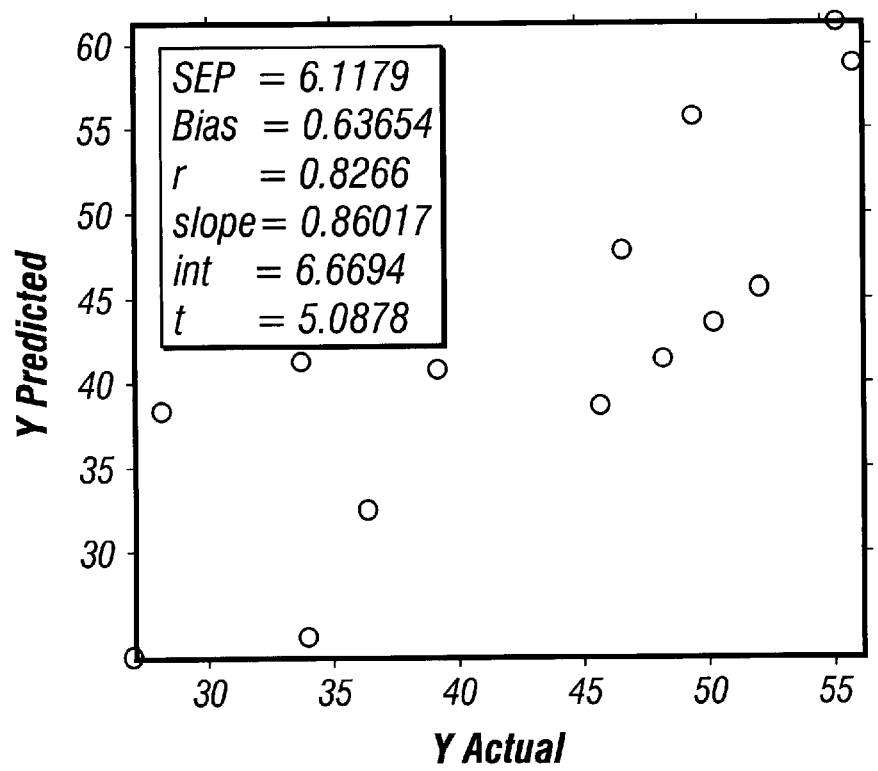

To demonstrate feasibility of the invented apparatus and method, the Experimental Data Set was analyzed using the previously described procedures. Outliers were removed using the outlier detection procedure previously described. Subsequently the data were preprocessed using MSC, followed by mean centering based on the mean of the emitting region of the filters based on their full width half maximum characteristics. The regions used were 1073–1087, 1175–1185, and 1275–1285 nm. Finally, MLR was applied to the data set. The calibration model was first developed using the samples of all four subjects, and subsequently validated using a "leave five out" cross-validation strategy. FIG. 7 shows a plot of actual corneometer measurements vs. estimations for the entire experimental data set. The standard error of estimation (SEE) for the experimental data set was 3.6995. Subsequently, a calibration model was developed and validated by using three subjects to develop the calibration model, and using the resulting model to predict SC hydration for the samples of the remaining subject. FIGS. 8 and 9 show plots of actual corneometer measurements vs. estimations for subjects four and three, respectively. The SEE was 4.2851 for subject four estimations and 6.1179 for subject three measurements.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. An apparatus for estimating a skin tissue property non-destructively, based on spectral measurements, comprising;
    means for measuring a spectrum at a selected skin tissue site on a subject;
    an estimation model developed from a calibration set of exemplary samples and independent measurement; and
    an analyzer, wherein processing is applied to said spectrum and said model subsequently applied to determine an estimate of said skin tissue property.

2. The apparatus of claim 1, wherein said spectral measurements comprises near IR (NIR) measurements.

3. The apparatus of claim 1, wherein spectral energy returned from said site is either transmitted through or reflected from said tissue site.

4. The apparatus of claim 1, wherein spectral energy returned from said site is diffusely reflected from said site.

5. The apparatus of claim 1, wherein said means for measuring a spectrum comprises:
    an energy source;
    means for separating energy into a plurality of targeted wavelengths, wherein said energy at said targeted wavelengths is transmitted to said skin tissue site;
    at least one sensor element, said sensor element adapted to detect energy returned from said skin tissue site as an analog signal and convert said detected energy to a current;
    means for converting said current to a voltage; and
    means for converting said voltage to a digital signal.

6. The apparatus of claim 5, wherein said energy source and said energy separating means together comprise a plurality of LED's, said LED's controlled by an LED driver and a master sequence.

7. The apparatus of claim 6, wherein said plurality of LED's comprises an LED array, each LED of said array producing energy centered at a specific targeted wavelength.

8. The apparatus of claim 6, wherein each of said plurality of LED's is successively illuminated.

9. The apparatus of claim 6, said LED driver controls current flow to each of said LED's.

10. The apparatus of claim 9, wherein said means for converting said current to a voltage comprises an analog front end.

11. The apparatus of claim 10, further comprising a phase modulating lock-in amplifier, wherein said voltage signal is received from said analog front end and a reference signal is received from said LED driver wherein said lock-in amplifier amplifies signals that are in phase with said reference signal so that the signal-to-noise ratio is increased, and a direct current output is supplied to a digitizing means.

12. The apparatus of claim 11, wherein said digitizing means comprises a 16-bit analog to digital converter.

13. The apparatus of claim 6, wherein an illumination interval for each LED is controlled according to parameters specified by said master sequence.

14. The apparatus of claim 6, wherein a sequence of illumination for said array is controlled according to parameters specified by said master sequence.

15. The apparatus of claim 6, wherein said LED's have a peak wavelength of approximately 1.07 µm, 1.22 µm, and 1.25 µm, respectively.

16. The apparatus of claim 15, wherein said LED array transmits energy in a wavelength range of approximately 700–2500 nm.

17. The apparatus of claim 6, wherein each of said LED's is equipped with an optical filter.

18. The apparatus of claim 17, wherein said filters have center wavelengths of approximately 1080 nm, 1180 nm, and 1280 nm respectively, wherein the full width half maximum of said filters ranges from approximately 11 to 14.8 nm.

19. The apparatus of claim 6, further comprising means for conducting energy from said energy source toward said measurement site.

20. The apparatus of claim 19, wherein said means for conducting energy comprises a plurality of illuminating fiber optics, each of said illuminating fiber optics having a probe end.

21. The apparatus of claim 20, further comprising a sample probe head and a reference probe head, said sample probe head comprising a subject interface, wherein said subject interface contacts said site, and wherein said reference probe head is adapted to collect a spectrum of a reference standard.

22. The apparatus of claim 21, wherein each LED has a plurality of associated illuminating fibers, wherein a first portion of said associated illuminating fibers couples said LED to said sample probe head and a second portion of said illuminating fibers couples said LED to said reference probe head.

23. The apparatus of claim 22, wherein said sample probe head comprises the probe ends of said first portion of associated illuminating fibers for each LED, and the probe ends of a plurality of detecting fibers, wherein said detecting fibers surround said illuminating fibers, wherein said probe ends form a closed, packed arrangement.

24. The apparatus, of claim 22, wherein said reference probe head comprises the probe ends of said second portion of illuminating fibers for each LED and a plurality of detection fibers, wherein said probe ends form a closed packed arrangement such that said detecting fibers completely surround each of said illuminating fibers.

25. The apparatus of claim 6, wherein said sensor element comprises one or more detectors.

26. The apparatus of claim 25, wherein said detectors comprise InGaAs detectors, and wherein an illuminating surface of said LED's comprises a point of illumination, and a detecting surface of said InGaAs detectors comprises a point of detection, and wherein a distance from a point of illumination to a point of detection is approximately 40 µm–1 mm.

27. The apparatus of claim 6, wherein said means for directing energy transmitted or reflected from said tissue measurement site and said reference toward said detecting means comprises a plurality of detecting fiber optics, each of said detecting fiber optics having a probe end, and wherein said detection fiber optics radially surround said LED's at specific distances.

28. The apparatus of claim 6, wherein said analyzing means comprises a processor programmed to perform said processing and said estimate determination, said processor including a power supply and an attached display device for displaying said estimate or a message indicating an invalid scan.

29. The apparatus of claim 28, wherein said master sequence is executed on said processor and said power supply supplies current to said LED's through said LED driver.

30. The apparatus of claim 28, wherein Said processing includes any of:

absorbance calculation;

preprocessing; and outlier detection.

31. The apparatus of claim 5, wherein said energy source comprises one of: an LED array and a quartz halogen lamp.

32. The apparatus of claim 5, wherein said separating means comprises one of a monochromator, a spectrometer, a spectrograph, an interferometer, and successive illumination through the elements of an LED array.

33. The apparatus of claim 5, wherein said energy is transmitted to said site through one of:

direct illumination;

a light pipe;

one or more fiber optics;

a lens system; and a light directing mirror system.

34. The apparatus of claim 5, wherein said sensor element comprises one or more detectors, said detectors responsive to a plurality of targeted wavelengths.

35. The apparatus of claim 5, further comprising means for directing said returned energy, said means for directing comprising one of:

one or more optical detectors; and one or more fiber optics.

36. The apparatus of claim 5, wherein said converting means comprises one or more analog circuits.

37. The apparatus of claim 5, wherein said digitizing means comprises an analog-to-digital converter.

38. The apparatus of claim 5, wherein said analyzer comprising a data-processing system programmed to perform said analysis.

39. The apparatus of claim 5, further comprising a reference standard.

40. The apparatus of claim 39, wherein processing includes absorbance calculation through a reference spectrum.

41. The apparatus of claim 39, wherein said reference standard is external to the remainder of said apparatus.

42. The apparatus of claim 39, wherein said reference standard is internal to said apparatus.

43. The apparatus of claim 42, wherein said source comprises an LED array.

44. The apparatus of claim 1, said property comprising hydration of living tissue.

45. The apparatus of claim 1, said property comprising stratum corneum hydration.

46. The apparatus of claim 1, wherein said means for measuring a spectrum comprises:

a polychromatic light source, wherein polychromatic light is transmitted to said tissue site;

means for separating polychromatic light returned from said site into a plurality of targeted wavelengths;

at least one sensor element, said sensor element adapted to detect light at said plurality of targeted wavelengths as an analog signal and convert said detected light to a current;

means converting said current to a voltage; and means for converting said voltage to a digital signal.

47. The apparatus of claim 1, wherein said model is based on one of:
multiple linear regression;
principal component regression; and
partial least squares regression.

48. The apparatus of claim 1, said tissue property comprising one of:
body fat;
body composition;
thickness of subcutaneous layer;
chronological age of a subject;
photo-aging of skin;
photo-damage to skin;
skin temperature;
skin thickness;
body fat;
skin cancer detection;
blood volume estimation;
tissue circulation and rate of perfusion;
tissue turgor;
tissue elasticity;
tissue edema;
sex determination;
dermal hydration;
epidermal hydration
tissue deformity;
tissue cholesterol;
Sweat;
free and bound water;
orientation of collagen fibers; and
tissue analyte determination, analytes including at least one of: glucose, cholesterol, triglycerides, sodium, urea, elastin and collagen.

* * * * *